United States Patent [19]

Law et al.

[11] Patent Number: 5,004,661

[45] Date of Patent: Apr. 2, 1991

[54] PHOTOCONDUCTIVE MEMBER HAVING SYMMETRICAL AND UNSYMMETRICAL SQUARAINE COMPOSITIONS

[75] Inventors: Kock-Yee Law, Fairport; F. Courtney Bailey, Webster, both of N.Y.

[73] Assignee: Xerox Corporation, Stamford, Conn.

[21] Appl. No.: 358,930

[22] Filed: May 30, 1989

[51] Int. Cl.$^5$ .............................. G03G 5/06
[52] U.S. Cl. ............................ 430/59; 430/73; 430/74; 430/126
[58] Field of Search ............ 430/59, 58, 73, 74, 430/126

[56] References Cited

U.S. PATENT DOCUMENTS

| | | | |
|---|---|---|---|
| 4,524,219 | 6/1985 | Law | 564/307 |
| 4,524,220 | 6/1985 | Law | 564/307 |
| 4,585,895 | 4/1986 | Law | 564/307 |
| 4,624,904 | 11/1986 | Kazmaier et al. | 430/59 |
| 4,707,427 | 11/1987 | Tanaka et al. | 430/59 |

FOREIGN PATENT DOCUMENTS 62249952  4/1979  Japan .

Primary Examiner—John Goodrow
Attorney, Agent, or Firm—E. O. Palazzo

[57] ABSTRACT

A process for the preparation of squaraines which comprises a cycloaddition, reductive alkylation and condensation reaction wherein there is reacted a nitroarylacetyl halide with a tetraalkoxy olefin, and a trialkylamine in a solvent; followed by the reaction of the resulting nitroaryl dione with hydrogen in the presence of an aldehyde and a catalyst in a solvent; and thereafter reacting the formed dialkylaminoaryl hydroxycyclobutene dione with N,N-dialkylaniline in an alcohol.

23 Claims, 3 Drawing Sheets

PHOTOCONDUCTIVE MEMBER HAVING SYMMETRICAL AND UNSYMMETRICAL SQUARAINE COMPOSITIONS

BACKGROUND OF THE INVENTION

This invention is generally directed to processes for the preparation of squaraine compositions, and more specifically to economical processes for the preparation of symmetrical and unsymmetrical squaraines wherein the selection of the costly squaric acid reactant is avoided. In one embodiment, the present invention is directed to the preparation of unsymmetrical and/or symmetrical squaraines by a cycloaddition, reductive alkylation and condensation method thereby avoiding the use of costly squaric acid as a reactant. In another embodiment of the present invention, there are provided symmetrical, or unsymmetrical squaraines with improved xerographic properties, inclusive of high charge acceptance, low dark decay, high photosensitivity, and improved cyclic stability when these compositions are incorporated into photoconductive imaging members. Also, in another embodiment of the invention of the present application there are provided imaging members with photoconductive layers comprised of the squaraines obtained with the processes illustrated herein, and charge or hole transport layers, especially those comprised of aryl amines, which members are sensitive to light in the wavelength region of from about 400 to about 1,000 nanometers. Therefore, the resulting members are responsive in some embodiments to visible light, and infrared illumination originating from laser printing apparatuses wherein, for example, gallium arsenide diode lasers are selected. The photoresponsive imaging members of the present invention can also, for example, contain situated between a photogenerating layer and a hole transporting layer, or situated between a photogenerating layer and a supporting substrate with a charge transport layer in contact with the photogenerating layer, a photoconductive component comprised of the unsymmetrical squaraines illustrated herein.

Numerous different xerographic photoconductive members, including squaraines and processes thereof, are known including, for example, or a composite layered device containing a dispersion of a photoconductive composition. An example of one type of composite xerographic photoconductive member is described, for example, in U.S. Pat. No. 3,121,006, wherein there are disclosed finely divided particles of a photoconductive inorganic compound dispersed in an electrically insulating organic resin binder. Also, layered photoresponsive devices including those comprised of separate generating layers and transport layers are described in U.S. Pat. No. 4,265,990, the disclosure of which is totally incorporated herein by reference, and overcoated photoresponsive materials containing a hole injecting layer, overcoated with a hole transport layer, followed by an overcoating of a photogenerating layer, and a top coating of an insulating organic resin are illustrated in U.S. Pat. No. 4,251,612. Examples of photogenerating layers disclosed in these patents include trigonal selenium and phthalocyanines, while examples of transport layers include certain aryl amines as mentioned therein. Also, there is illustrated in U.S. Pat. No. 4,415,639, the disclosure of which is totally incorporated herein by reference, the use of known squaraine compositions, such as hydroxy squaraines, as a photoconductive layer in an infrared sensitive photoresponsive device. More specifically, there is described in this patent an improved photoresponsive device containing a substrate, a hole blocking layer, an optional adhesive interfacial layer, an inorganic photogenerating layer, a photoconductive composition capable of enhancing or reducing the intrinsic properties of the photogenerating layer, which photoconductive composition is selected from various squaraine compositions, including hydroxy squaraine compositions, and a hole transport layer. Other patents disclosing photoconductive devices with squaraines, and processes for the preparation thereof usually with squaric acid are U.S. Pat. Nos. 4,471,041; 4,507,480; 4,390,610; 4,353,971 and 4,391,888.

There are illustrated in U.S. Pat No. 4,624,904, the disclosure of which is totally incorporated herein by reference, photoconductive imaging members with unsymmetrical hydroxy squaraine compositions, and aryl amine hole transport layers. The aforementioned unsymmetrical squaraine compounds can be obtained, for example, by the initial preparation of an aryl cyclobutenedione intermediate, followed by the reaction thereof with a substituted aniline. More specifically, with respect to method A illustrated in the '904 patent, the aryl cyclobutenedione is prepared by heating with reflux at a temperature of from about 40° to 50° C., depending on the solvent selected; about 20 millimoles to about 50 millimoles of substituted aniline; from about 60 millimoles to about 150 millimoles of dihalocyclobutenedione; and from about 100 milliliters to about 1,000 milliliters of a Fredal Craft solvent inclusive of, for example, carbon disulfide nitrobenzene or methylene chloride. This reaction is accomplished in the presence of from about 200 to about 900 millimoles of a catalyst such as aluminum chloride, and the resulting substituted aniline is reacted with a hydroxy substituted aniline in the presence of an aliphatic alcoholic solvent. Subsequent to separation, there are obtained the desired unsymmetrical squaraine compounds of the formula as detailed on page 8, beginning at line 10, for example.

Additionally, there are disclosed in a number of patents processes for preparing squaraine compositions. For example, in U.S. Pat. No. 4,524,220 there is illustrated a squaraine process by the reaction of squaric acid, and an aromatic aniline in the presence of an aliphatic amine. Also, in U.S. Pat. No. 4,524,219 there is described a process for the preparation of squaraines by the reaction of an alkyl squarate, and an aniline in the presence of an aliphatic alcohol and an optional acid catalyst. Moreover, disclosed in U.S. Pat. No. 4,524,218 are processes for the preparation of squaraines by the reaction of squaric acid with an aromatic amine, and a composition selected from the group consisting of phenols and phenol squaraines, which reaction is accomplished in the presence of an aliphatic alcohol and an optional azeotropic catalyst. Other processes for preparing squaraines are illustrated in U.S. Pat. No. 4,525,592, wherein there is described the reaction of a dialkyl squarate, and an aniline in the presence of an aliphatic alcohol and an acid catalyst.

Other references of interest include U.S. Pat. Nos. 3,617,270; 3,824,099; 4,175,956; 4,486,520; 4,508,803; 4,585,895; 4,521,621; 4,559,286; 4,552,286; 4,552,822 and 4,624,904.

As a result of a patentability search, there were selected U.S. Pat. No. 4,585,895 and Japanese 62-249952, which discloses the use of hydroxycyclo-butenedione derivatives as synthetic intermediates for squarylium compounds.

In U.S. Pat. No. 4,521,621, the disclosure of which is totally incorporated herein by reference, there are described photoresponsive imaging members containing unsymmetrical squaraines comprised by forming a mixture of squaric acid, a primary alcohol, a first tertiary amine, and a second tertiary amine. Also, in U.S. Pat. No. 4,886,722, the disclosure of which is totally incorporated herein by reference, a cycloaddition-condensation reaction for the preparation of certain squaraines is illustrated. More specifically, there is illustrated in the aforementioned patent the preparation of unsymmetrical squaraines by condensing, for example, a 1-alkoxyaryl-2-hydroxycyclobutene-3,4-dione derivative with an N,N-dialkylaniline derivative, such as 1-3′, 4′-dimethoxy-phenyl-2-hydroxycyclobutene-3,4-dione and 3-fluoro-N,N-dimethylaniline in a molar ratio of about 1 to 6, and preferably in a ratio of about 1 to 3 in the presence of an aliphatic alcohol, such as propanol, and an optional drying reagent. About 500 milliliters of alcohol per 0.1 moles of 1-alkoxyaryl-2-hydroxycyclobutene-3,4-dione are selected, however, up to about 1,000 milliliters of alcohol to about 0.5 to 1 moles of 1-alkoxyaryl-2-hydroxycyclobutene-3,4-dione can be selected. The drying reagent can be heterogeneous such as molecular sieves or homogeneous such as a trialkyl orthoformate. A ratio of 1 to 10 equivalents of drying reagent, more specifically tributyl orthoformate, can be used with a ratio of about 1 to 4 to the cyclobutene dione being preferred. Also, the reaction is generally accomplished at a temperature of about 60° C., to about 130° C., and preferably at a temperature of 70° C. to about 100° C. with stirring until the reaction is completed. Subsequently, the desired product can be isolated from the reaction mixture by known techniques such as filtration, and the product identified by analytical methods including IR, NMR, and mass spectrometry. Further, carbon, hydrogen, and nitrogen elemental analysis can be selected for aiding the identification of the product.

Although the above squaraines, and processes thereof are suitable for their intended purposes, there continues to be a need for other processes. More specifically, there remains a need for simple, economical processes for preparing certain symmetrical, or unsymmetrical squaraines with stable properties, which when incorporated into photoconductive devices result in reduced dark decay characteristics, and increased charge acceptance values as compared to substantially similar squaraine imaging members. Moreover, there remains a need for processes that enable the preparation of unsymmetrical and symmetrical squaraines wherein the use of costly squaric acid component reactants are avoided. In addition, there remains a need for photoconductive imaging members with certain stable electrical characteristics, that is for example the aforementioned imaging members are electrically stable for over 100,000 xerographic imaging cycles. In addition, imaging members with the aforementioned squaraines of the present invention are sensitive to a broad range of wavelengths, including visible and infrared light, such as of from about 400 to 900 nanometers, enabling such members to be useful in electrophotographic imaging and printing process including, for example, processes wherein diode lasers are selected.

SUMMARY OF THE INVENTION

It is therefore an object of the present invention to provide processes for the preparation of squaraines.

In another object of the present invention there are provided improved processes for preparing squaraine compositions, which when incorporated into photoresponsive imaging members posses, in many embodiments, excellent dark decay properties, high charge acceptance values, and electrical stability.

In yet another object of the present invention there are provided simple, economical processes for preparing symmetrical or unsymmetrical squaraine compositions or mixtures thereof, which can be selected for layered photoconductive imaging members containing charge transport layers comprised, for example, of aryl amines.

A further object of the present invention resides in improved processes for obtaining squaraine compositions of excellent sensitivity, and excellent cyclic stability when incorporated into layers imaging members with hole transport molecules.

Further, in another object of the present invention there are provided photoconductive imaging members with certain squaraines, which members are simultaneously responsive to infrared light and to visible light.

Also, in another object of the present invention there are provided processes for the preparation of squaraines wherein costly squaric acid is avoided as a reactant.

Additionally, another object of the present invention resides in the provision of imaging and printing methods with the photoconductive imaging members described herein.

Moreover, in another object of the present invention squaraines are prepared by a cycloaddition, reductive alkylation, and condensation reaction.

These and other objects of the present invention are accomplished by the provision of processes for the preparation of squaraines. More specifically, the process of the present invention comprises a cycloaddition, reductive alkylation and condensation method. In one specific embodiment, the present invention is directed to processes for the preparation of squaraines which comprises the initial preparation of a nitroaryl halide, such as a nitrophenylacetyl halide. Thereafter, there is prepared from the halide a nitroaryldione, such as nitrophenyl hydroxycyclobutene dione. From the dione there is prepared an amino hydroxycyclobutene dione, which dione is selected for the preparation of the desired symmetrical, or unsymmetrical squaraines.

The process of the present invention in an embodiment comprises a cylcoaddition, reductive alkylation and condensation method as illustrated in the general and specific reaction schemes of FIGS. 1 and 2, wherein X and Y are independently selected from the group consisting of hydrogen, halide, including chlorine, fluoride, bromide, iodine; alkyl, especially alkyl with from 1 to about 25 carbon atoms and preferably from 1to about 20 carbon atoms, alkyl with from 1 to 25 carbon atoms and preferably about 1 to about 20 carbon atoms; hydroxy; and the like; n and m are numbers of from 0 (zero) to about 4 and preferably are 0, 1 or 2; and R, R′, R″ and R‴ are independently selected from alkyl groups, and the like. Examples of alkyl and alkoxy include methyl, methoxy, ethyl, ethoxy, propyl, propoxy, butyl, butoxy, pentyl, pentoxy, heptyl, heptoxy, nonyl, nonoxy, and the like. Aryl includes those groups with, for example, 6 to about 24 carbon atoms, such as phenyl, naphthyl and the like.

With the present invention there is provided a process for the preparation of squaraines which comprises (1) a cylcoaddition, reductive alkylation and condensation reaction wherein there is reacted a nitroarylacetyl halide with a tetraalkoxy olefin, and trialkylamine in a solvent; (2) followed by the reaction of the resulting nitroaryl dione with hydrogen in the presence of an aldehyde and a catalyst in a suitable solvent; and (3) thereafter reducing the formed dialkylaminoaryl hydroxycyclobutene dione with N,N-dialkylaniline in an alcohol.

The symmetrical and unsymmetrical compositions of the present invention are thus generally prepared by a cycloaddition, reductive alkylation and condensation reaction. More specifically, in a specific embodiment the squaraines can be prepared, reference step (3) above, by condensing, for example, a 1-p-dialkylaminoaryl-2-hydroxycyclobutene-3,4-dione with an N,N-dialkylaniline derivative, such as 1-p-dimethylaminophenyl-2-hydroxycyclobutene-3,4-dione and N,N-dimethylaniline in a molar ratio of about 1 to 6, and preferably in a ratio of about 1 to 3 in the presence of an aliphatic alcohol, such as ethanol, butanol, methanol, propanol, and an optional drying reagent. Depending on the reactants selected from other factors, about 1 liter of alcohol per 0.1 mole of 1-dialkylaminoaryl-2-hydroxycyclobutene-3,4-dione is selected. However, up to 5 to 10 liters of alcohol per 0.1 to 0.5 mole of 1-dialkylaminoaryl-2-hydroxycyclobutene-3,4-dione can be selected. Optionally, the 1-dialkylaminoaryl-2-hydroxycyclobutene-3,4-dione may be introduced to the alcoholic reaction mixture as a DMF (dimethylformamide), a DMSO (dimethylsulfoxide) solution, or as pure solid. The drying reagent can be heterogeneous, such as molecular sieves or homogeneous, such as a trialkyl orthoformate. A ratio of 1 to 10 equivalents of drying reagent, and more specifically tributyl orthoformate can be used with a ratio of about 1 to 4 to the cyclobutene dione being preferred. Also, the condensation reaction is generally accomplished at a temperature of from about 60° C. to about 130° C., and preferably at a temperature of 70° C. to about 100° C. with stirring until the reaction is completed. Subsequently, the desired squaraine product can be isolated from the mixture by known techniques such as filtration, and this product can be identified by analytical tool including IR and mass spectrometry. Further, carbon, hydrogen, nitrogen elemental analysis can be selected for aiding the identification of the product.

The 1-p-dialkylaminoaryl-2-hydroxycyclobutene-3,4-dione or other dione reactant can be prepared by a reductive alkylation process. Specifically, 1-p-dialkylaminoaryl-2-hydroxyclocybutene-3,4-dione can be prepared by reducing the nitro cyclobutene dione with hydrogen in the presence of a catalyst, such as Palladium on carbon, and in the presence of an aldehyde. The temperature of the reductive alkylation process can, for example, be at about 20° C. to about 100° C. with 30° to 75° C. being preferred. The solvent for this aspect of the process can be DMF or DMSO or any solvent in which both the reactant and product are soluble. The concentration of Palladium that can be selected is from 1 to about 20 percent with 10 percent being preferred, although other effective concentrations can be selected. The aldehyde can be selected, for example, from the group consisting of formaldehyde, acetaldehyde and butyaldehyde. The ratio of the nitroaryl cyclobutene dione to aldehyde can be from about 2 to about 100 with 2 to 20 being preferred, although other effective concentrations can be selected. The pressure of the hydrogen selected for the reductive alkylation process is usually, but is not limited to, about 10 to 100 psi with 20 to 80 psi being preferred.

The 1-p-nitroaryl-2-hydroxycyclobutene-3,4-dione selected in the reductive alkylation process is prepared by the known [2+2] cycloaddition process involving a tetraalkoxy olefin and a p-nitroaryl ketene generated in situ by the reaction of a p-nitroarylacetyl chloride or other halide and a base. Thus, for example, p-nitrophenylacetyl chloride can be reacted with tetraethoxyethylene in diethyl ether solvent in the presence of triethylamine. The ratio of acid chloride to tetraethoxyethylene is, for example, from about 1 to 10 with 1 to 4 being preferred. The amount of triethylamine used will vary, however, usually an amount equivalent to the amount of the acid chloride is selected. Also, the above reaction mixture is stirred at room temperature (25° to 30° C.) until the reaction is completed. The [2+2] cycloadduct mixture can be hydrolyzed directly by refluxing in an aqueous hydrochloric acid solution. The hydrolyzed product is then purified by conventional techniques such as recrystallization, and the like. This results in 1-p-nitrophenyl-2-hydroxycyclobutene-3,4-dione, which can be reductive alkylated to from 1-p-dimethylaminophenyl-2-hydroxycyclobutene-3,4-dione, which can then be reacted with an N,N-dialkylaniline as described herein.

With the process of the present invention, there can be prepared, for example, the following and other squaraines

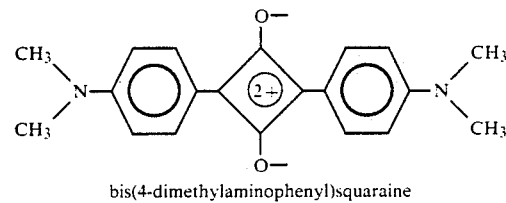

bis(4-dimethylaminophenyl)squaraine

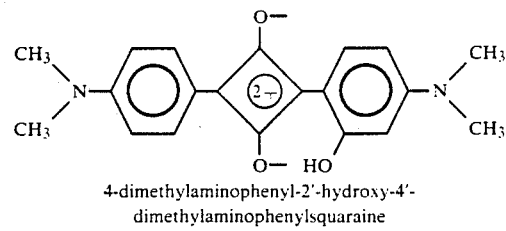

4-dimethylaminophenyl-2'-hydroxy-4'-dimethylaminophenylsquaraine

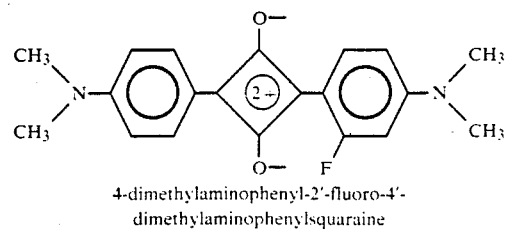

4-dimethylaminophenyl-2'-fluoro-4'-dimethylaminophenylsquaraine

-continued

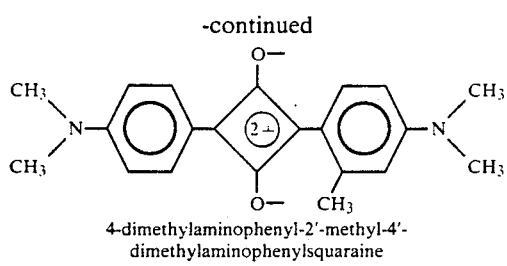
4-dimethylaminophenyl-2'-methyl-4'-dimethylaminophenylsquaraine

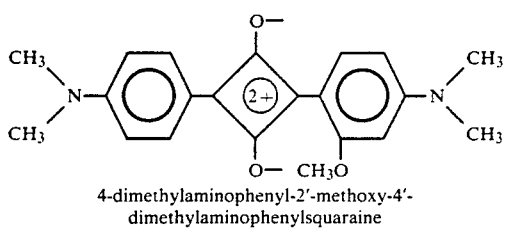
4-dimethylaminophenyl-2'-methoxy-4'-dimethylaminophenylsquaraine

The squaraine compounds obtained by the process for the present invention can be selected for various photoconductive imaging members. One such member is comprised of a supporting substrate, a hole transport layer, and as a photoconductive layer situated between the supporting substrate and the hole transport layer the squaraines prepared in accordance with the process of the present invention. Also, in another embodiment, there is envisioned a layered photoresponsive device comprised of a supporting substrate, a photoconductive layer comprised of the squaraine compound obtained by the process of the present invention; and situated between the supporting substrate and the photoconductive layer a hole transport layer. In one specific illustrative embodiment, the photoresponsive device can be comprised of (1) a supporting substrate, (2) a hole blocking layer, (3) an optional adhesive interface layer, (4) a squaraine photogenerating layer, and (5) a hole transport layer. THus, a specific photoresponsive device of the present invention can be comprised of a conductive supporting substrate, a hole blocking metal oxide layer in contact therewith, an adhesive layer, a squaraine photogenerating material obtained by the process of the present invention and overcoated on the optional adhesive layer; and as a top layer, a hole, or charge transport layer comprised of certain aryl amines, reference for example U.S. Pat. No. 4,265,990, the disclosure of which is totally incorporated herein by reference, dispersed in a resinous matrix. The photoconductive layer composition, when in contact with the hole transport layer, is capable of allowing holes generated by the photogenerating layer to be transported.

The photoresponsive devices described herein can be incorporated into various imaging systems such as those conventionally known as xerographic imaging processes. Additionally, the imaging members of the present invention can be selected for imaging and printing systems with visible light and/or infrared light. In this embodiment, the photoresponsive devices may be respectively, negatively charge, exposed to light in a wavelength of from about 400 to 900 nanometers, either sequentially or simultaneously, followed by developing the resulting image and transferring to paper.

BRIEF DESCRIPTION OF THE DRAWINGS

For a better understanding of the features of the present invention, the following detailed description of various preferred embodiments is provided, wherein.

DESCRIPTION OF THE PREFERRED EMBODIMENTS

Preferred embodiments of the invention will now be illustrated, it being noted that substantially equivalent imaging members are also embraced within the scope of the present invention.

Figure 3:
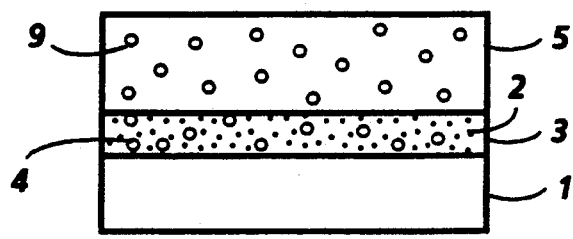
FIGS. 3, 4 and 5 represent imaging members of the present invention.

FIG. 3 illustrates a photoconductive imaging member of the present invention comprising a supporting substrate 1, a photogenerating layer 3 comprising an unsymmetrical squaraine 2 obtained by the process of the present invention optionally dispersed in a resinous binder composition 4, and a charge carrier hole transport layer 5, which comprises a hole transporting molecule dispersed in an inactive resinous binder composition 9.

Figure 4:
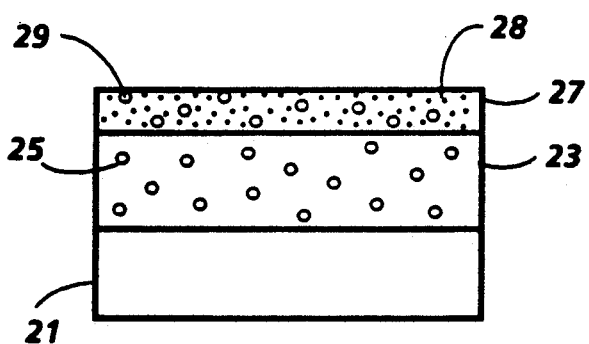

FIG. 4 illustrates essentially the same member as that shown in FIG. 3 with the exception that the hole transport layer is situated between the supporting substrate and the photogenerating layer. More specifically, this figure illustrates a photoconductive imaging member comprising a supporting substrate 21, a hole transport layer 23 comprising an aryl amine charge or hole transport composition dispersed in an inactive resinous binder composition 25, and a photogenerating layer 27 comprising an unsymmetrical squaraine 28 obtained by the process of the present invention optionally dispersed in a resinous binder composition 29.

Figure 5:
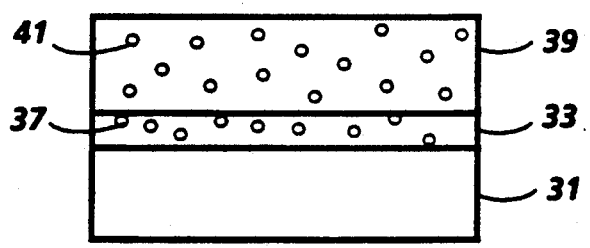

FIG. 5 illustrates a photoconductive imaging member of the present invention comprising a supporting substrate 31, a photogenerating layer 33 comprising the unsymmetrical squaraine 4-dimethylaminophenyl-2'-hydroxy-4'-dimethylaminophenyl squaraine or the symmetrical squaraine bis(4-dimethylaminophenyl) squaraine obtained by the process of the present invention optionally dispersed in a resinous binder composition 37, and a charge carrier hole transport layer 39, which comprises a hole transporting molecule dispersed in an inactive resinous binder composition 41.

The supporting substrate of the imaging members may comprise an insulating material such as an inorganic or organic polymeric material, including Mylar ®, a commercially available polymer; a layer of an organic or inorganic material having a semiconductive surface layer such as indium tin oxide or aluminum arranged thereon; or a conductive material such as aluminum, titanium, chromium, nickel, brass, or the like. The substrate may be flexible or rigid and may have a number of different configurations, such as a plate, a cylindrical drum, a scroll, an endless flexible belt, and the like. Preferably, the substrate is in the form of an endless flexible belt. In some situations, it may be desirable to coat an anticurl layer, such as polycarbonate materials commercially available as Makrolon ®, on the back of the substrate, particularly when the substrate is an organic polymeric material.

The thickness of the substrate layer depends on many factors, including economic considerations. Thus, this layer may be of substantial thickness, for example over 100 mils, or of minimal thickness provided that there are no adverse effects on the system. In a preferred embodiment, the thickness of this layer is from about 3 mls to about 10 mils.

Generally, the squaraine photoconductive layer has a thickness of from about 0.05 micron to about 10 microns or more, and preferably has a thickness of from about 0.1 micron to about 3 microns. The thickness of this layer, however, is dependent primarily upon the photogenerating weight loading, which may vary from about 5 to about 100 percent. Generally, it is desirable to provide this layer in a thickness sufficient to absorb about 90 percent or more of the incident radiation which is directed upon it in the imagewise or printing exposure step. The maximum thickness of this layer is dependent primarily upon factors such as mechanical considerations, the specific squaraine compound selected, the thicknesses of the other layers, and whether a flexible photoconductive imaging member is desired.

The hole transport layer comprises various materials that are capable of transporting charges such as an aryl amine compound dispersed in a resinous binder. Preferred aryl amine compounds include those of the formula:

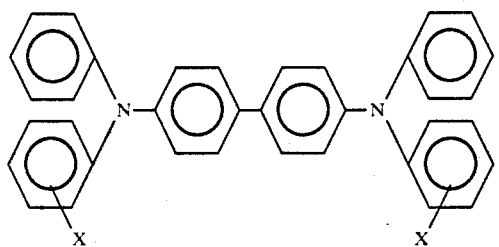

wherein X is selected from the group consisting of alkyl and halogen. Preferably, X is selected from the group consisting of methyl and chloride in either the ortho, meta, or para positions. Suitable inactive binder materials for the hole transport layer include known highly insulating resins, which generally have a resistivity of at least $10^{12}$ ohm-cm to prevent undue dark decay. The insulating resin becomes electrically active when it contains from about 10 to about 75 percent by weight of the substituted N,N,N', N''-tetraphenyl[1,1-biphenyl]4-4'-diamines corresponding to the foregoing formula. Compounds encompassed by, or corresponding to the above formula include N,N'-diphenyl-N,N'-bis(alkylphenyl)-[1,1-biphenyl]-4,4'-diamine, wherein alkyl is selected from the group consisting of methyl, such as 2-methyl, 3-methyl and 4-methyl, ethyl, propyl, butyl, hexyl, and the like. With halo substitution, the amine is N,N'-diphenyl-N,N'-bis(halo phenyl)-[1,1'-biphenyl]-4,4'-diamine, wherein halo is 2-chloro, 3-chloro or 4-chloro. Other electrically active small molecules that can be dispersed in the electrically inactive resin to form a layer which will transport holes include bis(4-diethylamino-2-methylphenyl)phenyl methane, 4', 4''-bis(-diethylamino)-2',2'''-dimethyltriphenyl methane, bis-4-(diethylaminophenyl)phenyl methane, and 4',4'-bis(diethylamino)2,2'-dimethyltriphenyl methane. Generally, the hole transport layer has a thickness of from about 5 to about 75 microns, and preferably of from about 10 to about 40 microns.

Examples of the highly insulating and transparent resinous components or inactive binder resinous material for the transport layer include materials such as those described in U.S. Pat. No. 3,121,006, the disclosure of which is totally incorporated herein by reference. Specific examples of suitable organic resinous materials include polycarbonates, acrylate polymers, vinyl polymers, cellulose polymers, polyesters, polysiloxanes, polyamides, polyurethanes and epoxies as well as block, random or alternating copolymers thereof. Preferred electrically inactive binder materials are polycarbonate resins having a molecular weight of from about 20,000 to about 100,000 with a molecular weight in the range of from about 50,000 to about 100,000 being particularly preferred. Generally, the resinous binder contains from about 10 to about 75 percent by weight of the active material corresponding to the foregoing formula, and preferably from about 35 percent to about 50 percent of this material.

Similar binder materials may be selected for the squaraine photogenerating layer, including those illustrated in U.S. Pat. No. 3,121,006, the disclosure of which is totally incorporated herein by reference. A preferred class of binder materials for the squaraine photogenerating layer is a poly(vinyl acetal).

The photoconductive imaging member of the present invention may optionally contain a hole blocking layer situated between the supporting substrate and the photogenerating layer. This layer may comprise metal oxides with a thickness of from about 300 to about 1,000 Angstroms, such as aluminum oxide or nylon (thickness of from about 0.05 to about 3 microns), and the like, or materials such as organo silanes with a thickness of from about 50 to about 300 Angstroms. The primary purpose of this layer is to prevent hole injection from the substrate during and after charging. Typically, this layer is of a thickness of less than 50 Angstroms, although it may be as thick as 1 micron in some instances.

In addition, the photoconductive imaging member may also optionally contain an adhesive interface layer situated between the hole blocking layer and the photogenerating layer. This layer may comprise a polymeric material such as polyester, polyvinyl butyral, polyvinyl pyrrolidone and the like. Typically, this layer is of a thickness of less than about 0.6 micron.

Imaging members of the present invention exhibit superior xerographic properties. For example, values for dark development potential ($V_{ddp}$) range from about −400 to about −1000. Preferred ranges for dark development potential for the imaging members of the present invention are usually about −500 to −900 volts with −800 volts being especially preferred. High dark development potentials permit high contrast potentials, which result in images of high quality with essentially no background development.

The imaging members of the present invention also exhibit low dark decay values of about −50 volts per second or less. Low dark decay values are of importance for developing high quality images since dark decay measures the amount of charge that disappears after charging of the photoreceptor, and a large difference in charge between exposed and unexposed areas of the photoreceptor results in images with desirable high contrast. Acceptable values for dark decay vary depending on the design of the imaging apparatus in which the imaging members are contained. This dark decay may be as high as −100 volts per second with −50 volts, and −10 to −20 volts per second being preferred.

Residual potential values ($V_R$) for the imaging members of the present invention are also superior, ranging from about −5 volts to −50 volts. Residual potential is a measure of the amount of charge remaining on the imaging member after erasure by exposure to light and prior to imaging. Residual potentials of −5 to −10 are considered exceptional. Photosensitivity values ($E_{0.5ddp}$ at 600 nanometers) for the imaging members of the present invention are excellent, and are from about 10 to 20 ergs per square centimeter.

The present invention also encompasses a method of generating images with the photoconductive imaging members disclosed herein. One method comprises, for example, the steps of generating an electrostatic image on a photoconductive imaging member of the present invention, subsequently developing the electrostatic image with known developer compositions comprised of resin particles, pigment particles, additives, including charge control agents and carrier particles, reference U.S. Pat. Nos. 4,558,108; 4,560,535; 3,590,000; 4,264,672; 3,900,588 and 3,849,182, the disclosures of each of these patents being totally incorporated herein by reference, transferring the developed electrostatic image to a suitable substrate, and permanently affixing the transferred image to the substrate. Development of the image may be achieved by a number of methods, such as cascade, touchdown, powder cloud, magnetic brush, and the like. Transfer of the developed image to a substrate may be by any method, including those wherein a corotron or a biased roll is selected. The fixing step may be performed by means of any suitable method, such as flash fusing, heat fusing, pressure fusing, vapor fusing, and the like.

The following examples are being supplied to further define various species of the present invention, it being noted that these examples are intended to illustrate and not limit the scope of the present invention. Parts and percentages are by weight unless otherwise indicated.

EXAMPLE I

Para (p)-nitrophenylacetic acid (60.6 grams) and phosphorus pentachloride (74.4 grams) were charged into a 1 liter neck reaction flask. The aforementioned two solid compounds were mixed gently with a glass rod and an exothermic reaction was observed which was accompanied by the formation of phosphorus oxychloride. When the exotherm subsided, the formed mixture was brought to reflux at an oil-bath temperature of about 120° C. for about 2 hours. The resulting mixture was then cooled to about 60° C. and phosphorus oxychloride was removed under reduced pressure. The crude product was then recrystallized from n-heptane (about 1.5 liters) to yield pure p-nitrophenylacetyl chloride (white solid), 53.6 grams, 83 percent; m.p. 47.5° to 49° C.

EXAMPLE II 1-p-nitrophenyl-2-hydroxycyclobutene-3,4-dione was synthesized by a [2+2] cycloaddition reaction similar to that reported by Bellus (*J. Chem. Soc.,* 100, 8026 (1978)), the disclosure of which is totally incorporated herein by reference.

Tetraethoxyethylene, which was freshly synthesized using the procedure of Bellus et al. (*Helv. Chim. Acta.,* 63, 1130 (1980)), (51.3 grams, 0.25 mole), the disclosure of which is totally incorporated herein by reference, triethylamine (54.8 grams), and diethyl ether solvent (1.6 liters) was charged into a 3liter three-neck flash which was equipped with a mechanical stir and a nitrogen inlet. An etheral solution containing 105.2 grams of the p-nitrophenylacetyl chloride of Example I in 800 milliliters of ether was added into the tetraethoxyethylene solution slowly at room temperature in a two hour period. A light brown precipitate was formed during the addition. The resulting product mixture was maintained at 25° to 30° C. by a warm water bath for 4 more hours. The product resulting, which was soluble in diethyl ether, was isolated by filtration. The formed insoluble precipitate was then washed with another liter of ether. After solvent evaporation, 83.2 grams of yellow residue was obtained. The yellow residue was then hydrolyzed with 150 milliliters, 18 percent of hydrochloric acid at reflux for 4.5 hours. Hydrochloric acid was evaporated under reduced pressure to yield 46.5 grams of crude product (a tan color gum). The crude product was then digested with boiling n-hexane and was recrystallized from a mixture of acetone and toluene. A light yellow solid, 1-p-nitrophenyl-2-hydroxycyclobutene-3,4-dione was obtained, yield 28.1 grams, 51 percent; m.p. 162° to 163° C. (dec.); IR(KRb): 1,822, 1,790 and 1,724 $cm^{-1}$, (C=O); NMR (DMSO—$d_6$) $\delta$ 8.05 to 8.4 ppm (AB quartlet); and MS (m/z): 219 (M+).

Analysis Calculated for $C_{12}H_{10}O_5$ C 54.81, H 2.30, N 6.39. Found: C 54.91, H 2.86, N 6.57.

EXAMPLE III

A solution containing 8.77 grams of the 1-p-nitrophenyl-2-hydroxycyclobutene-3,4-dione of Example II in 160 milliliters DMF (dimethylformamide) was placed in a 500 milliliter Parr bottle. Thereafter, 8.8 milliliters, 37 percent, of formaldehyde solution and 2.4 grams of catalyst (10 percent Palladium on carbon) were added. The Parr bottle was then placed on a Parr apparatus and the mixture was hydrogenated by hydrogen at a pressure of about 60 psi at about 50° C. for about 1.5 hours. The catalyst was removed by filtration and the solvent was evaporated under reduced pressure. The resulting orange-brown residue was then digested with acetone. After vacuum drying, 7.02 grams, 80.8 percent, the orange solid, 1-p-dimethylaminophenyl-2-hydroxycyclobutene-3,4-dione, was obtained. m.p.>300° C. (dec.); IR(KBr): 1,695 and 1,748 $cm^{-1}$, (C=O); $^1$HNMR (DMSO—$d_6$) $\delta$ 3.04, (s, 6H, NCH$_3$), b 6.86 (d, 2H, J=9.6 Hz) and 7.87 (d, 2H, J=9.6 Hz; and MS (m/z: 217 (M+).

Analysis Calculated for $C_{12}H_{11}NO_3$: C 66.35, H 5.10, N 6.45. Found: C 64.61, H 5.17, N 6.95.

EXAMPLE IV

Bis(4-dimethylaminophenyl) squaraine was prepared by reacting the 1-p-dimethylaminophenyl-2-hydroxycyclobutene-3,4-dione of Example III with N,N-dimethylaniline in refluxing 2-propanol in the presence of tributyl orthoformate. N,N-dimethylaniline, 0.35 milliliter, 2.76 millimoles), 25 milliliters of 2-propanol, and 2 milliliters of tributyl orthoformate were charged into a 100 milliliter 3-necked flask, which was equipped with a magnetic stir bar and a nitrogen inlet. The mixture was stirred and brought to reflux. A solution containing 1-(p-dimethylaminophenyl)-2-hydroxycyclobutene-3,4-dione, 0.3 gram, 1.38 millimoles, in about 4 milliliters of DMF was added slowly through a pressure equalizing funnel in a 3 hour period. After the addition was complete, the product mixture was kept at reflux for 3 more hours. The blue precipitate formed was isolated by filtration. After washing with methanol, ether and vacuum drying, 0.20 gram of blue solid, which was subsequently identified as bis(4-dimethylaminophenyl) squaraine, was obtained in a yield of 46 percent. m.p. 275° to 276° C.; IR(KBr): 1.588 $cm^{-1}$; and MS (m/z): 320 (M+), 322 (M+$H_2^{7+}$) and 334 (M+$CH_2^{7+}$).

Analysis Calculated for $C_{20}H_{20}N_2O_2$: C 74.98, H 6.29, N 8.74. Found: C 73.96, H 6.39, N 8.27.

EXAMPLE V

The process of Example IV was repeated with the exception that 3-hydroxy-N,N-dimethylaniline was selected in place of N,N-dimethylaniline, yielding 4-dimethylaminophenyl-2'-hydroxy-4'-dimethylaminophenylsquaraine, 0.24 gram, 52 percent. m.p. 286° to 287° C.; IR(KBr): 1,592 and 1,622 cm$^{-1}$; and MS (m/z): 336 (M+).

Analysis Calculated for $C_{20}H_{20}N_2O_3$: C 71.41, H 5.99, N 8.33. Found: C 70.52, H 5.95, N 8.44.

Example VI

The process of Example IV was repeated with the exception that 3-methyl-N,N-dimethylaniline was selected in place of N,N-dimethylaniline, yielding 4-dimethylaminophenyl-2'-methyl-4'-dimethylaminophenylsquaraine, 0.10 gram, 22 percent. m.p. 244° to 245° C.; IR(KBr): 1,590 cm$^{-1}$; and MS (m/z): 344 (M+), 336 (M+$H_2^{7+}$) and 348 (M+$CH_2^{7+}$).

Analysis Calculated for $C_{21}H_{22}N_2O_2$: C 75.43, H 6.63, N 8.38. Found: C 74.13, H 6.66, N 7.93.

EXAMPLE VII

The process of Example IV was repeated with the exception that 3-fluoro-N,N-dimethylaniline was selected in place of N,N-dimethylaniline, and a slightly larger reaction scale was used. Specifically, 3-fluoro-N,N-dimethylaniline, 0.46 gram, 4.6 millimoles, 42 milliliters of 2-propanol and 3.3 milliliters of tributyl orthoformate were charged into a 100 milliliter 3-necked reaction flask, which was equipped with a magnetic stir bar and a nitrogen inlet. The mixture was stirred and brought to reflux. A solution containing 1-p-dimethylaminophenyl-2-hydroxycyclobutene-3,4-dione of Example III (0.5 gram in 7 milliliters of DMF) was then added slowly through a pressure equalizing funnel in a 3 hour period. After the addition was complete, the product mixture was retained at reflux for 3 more hours. A blue precipitate was formed and was isolated by filtration. After washing with methanol, ether and vacuum drying, 0.03 gram of a blue solid, which was subsequently identified as 4-dimethylaminophenyl-2'-fluoro-4'-dimethylaminophenylsquaraine, was obtained in a yield of 3.8 percent. m.p.>270° C. (dec.); IR(KBr): 1,592 and 1,622 cm$^{-1}$; and MS (m/z): 352 (M+$CH_2^{7+}$).

Analysis Calculated for $C_{20}H_{19}N_2O_2F$: C 70.99, H 5.66, N 8.28. Found: C 69.88, H 5.73, N 7.75.

EXAMPLE VIII

The process of Example IV was repeated with the exception that 3-methoxy-N,N-dimethylaniline was selected in place of N,N-dimethylaniline yielding 4-dimethylaminophenyl-2'-methoxy-4'-dimethylaminophenylsquaraine, 0.27 gram, 33 percent. m.p. 229° C. (dec); IR(KBr): 1,590 cm$^{-1}$; and MS (m/z): 350 (M+).

Analysis Calculated for $C_{21}H_{22}N_2O_3$: C 71.98, H 6.33, N 7.99. Found: C 70.19, H 6.50, N 7.86.

EXAMPLE IX

The process of Example IV was repeated with the exception that 1-butanol was selected as the reaction solvent in place of 2-propanol yielding bis(4-dimethylaminophenyl)squaraine, 0.15 gram, 34 percent.

EXAMPLE X

The process of Example V was repeated with the exception that 1-heptanol was selected as a reaction solvent in place of 2-propanol, and the reaction was carried out at a reduced pressure (about 0.26 millimeter Hg) and at a bath temperature of about 140° C. yielding 4-dimethylaminophenyl-2'-hydroxy-4'-dimethylaminophenylsquaraine, 0.26 gram, 35 percent.

EXAMPLE XI

There was prepared a photoresponsive device or imaging member containing as the photoconductive material the squaraine as prepared in accordance with Example IV, and as a charge transport layer an aryl amine dispersed in a resinous binder. Specifically, there was prepared a photoresponsive device by providing a ball grained aluminum substrate of a thickness of 150 microns, followed by applying thereto with a multiple clearance film applicator, in a wet thickness of 0.5 mil, a layer of the organo silane N-methyl-3-aminopropyltrimethoxysilane, available from PCR Research Chemicals, Florida, in ethanol in a 1:20 volume ration. This layer was then allowed to dry for .5 minutes at room temperature, followed by curing for 10 minutes at 110° C., in a forced air oven.

A photoconductive layer containing 80 percent by weight of bis(4-dimethylaminophenyl)squaraine obtained by the process of Example IV, and 20 percent by weight of polyvinyl formal was then prepared as follows:

In a 2 ounce amber bottle, there was added 0.21 gram of the above squaraine, 0.05 gram of poly(vinyl formal) (obtained from Scientific Polymer Products, Inc.), formal content 82 percent, acetate content 12 percent, hydroxy content 6 percent, 85 grams of ⅛ inch stainless steel shots and 10 milliliters of methylene chloride. The above mixture was placed on a ball mill for 24 hours. The resulting slurry was then coated on an aluminum substrate using a 0.5 mil wet-gap Bird film applicator. The layer was then air dried for 5 minutes, and at 135° C. for 10 minutes in a forced air oven. The dry thickness of the squaraine layer was about 0.5 micron.

The above photoconductive layer was then overcoated with a charge transport layer, which was prepared as follows:

A transport layer composed of 50 percent by weight Makrolon ®, a polycarbonate resin available form Larbensabricken Bayer A.G., was mixed with 50 percent by weight of the aryl amine N,N'-bis(3-methylphenyl)-1,1'biphenyl-4,4'-diamine. This solution was mixed to 9 percent by weight in methylene chloride. All of these components were placed in an amber bottle and dissolved. The mixture was coated to provide a layer with a dry thickness of 30 microns over the above squaraine photoconductive layer using a multiple clearance film applicator (15 mils wet gap thickness). The resulting device was then air dried at room temperature for 20 minutes, followed by drying in a forced air oven at 135° C. for 6 minutes.

The above photoreceptor device was then incorporated into a xerographic imaging test fixture wherein latent images were generated on the photoreceptor. There resulted, subsequent to development of the images with toner particles containing a styrene n-butylmethacrylate resin, 88 percent, 10 percent of carbon black, and 2 percent by weight of the charge enhancing additive cetyl pyridinium chloride, images of excellent resolution and high quality with substantially no background deposits, after heat fixing to paper.

EXAMPLE XII

A photoconductive imaging member was prepared by providing a titanized Mylar substrate in a thickness of 3 mils and applying thereto a layer of silane as described in Example XI, and then a layer of 0.5 percent by weight of E. I. DuPont 49,000 adhesive in methylene chloride and 1,1,2-trichloroethane (4:1 volume ratio) with a Bird Applicator to a wet thickness of 0.5 mil. The layer was allowed to dry for one minute at room temperature, and 10 minutes at 100° C. in a forced air oven. The resulting layer had a dry thickness of 0.5 micron.

In a 2 ounce amber bottle, there was added 0.21 gram of 4-dimethylaminophenyl-2'-hydroxy-4'-dimethylaminophenylsquaraine, obtained from Example V, 0.05 gram of poly(vinyl butyral) (from Scientific Polymer Products, Inc.), butyral content 88 percent, acetate content 1 percent, hydroxy content 11 percent, 85 grams of ⅛ inch stainless steel shots and 10 milliliters methylene chloride. The above mixture was placed on a ball mill for 24 hours. The resulting slurry was then coated on the titanized Mylar substrate using a 1.0 mil wet-gap Bird Film Applicator. The layer was then air dried for 5 minutes and at 135° C. for 10 minutes in a forced air oven. The dry thickness of the squaraine layer was about 0.5 micron.

The above photoconductive layer was then overcoated with a charge transport layer, which was prepared as follows:

A transport layer composed of 50 percent by weight Makrolon ®, a polycarbonate resin available from Larbensabricken Bayer A.G., was mixed with 50 percent by weight N,N'-bis(3-methylphenyl)-1,1'-biphenyl-4,4'-diamine. This solution was mixed to 9 percent by weight in methylene chloride. All of these components were placed in an amber bottle and dissolved. The mixture was coated on the above squaraine photogenerating layer to provide a layer with a dry thickness of 30 microns, which coating was accomplished with a multiple clearance film applicator, 15 mils wet gap thickness. The resulting device was then air dried at room temperature for 20 minutes, followed by drying in a forced air oven at 135° C. for 6 minutes.

The above photoreceptor device was then incorporated into a xerographic imaging test fixture wherein latent images were generated on the photoreceptor. There resulted, subsequent to development of the images with toner particles containing a styrene n-butyl-methacrylate resin, 88 percent, 10 percent of carbon black, and 2 weight percent of distearyl dimethyl ammonium methyl sulfate charge enhancing additive, and fixing by heat images of excellent resolution, and high quality with substantially no background deposits after heat fixing to paper.

Further, photoresponsive devices can be prepared by repeating the procedure of Examples XI and XII with the exception that there was selected as the squaraine photogenerator 4-dimethylaminophenyl-2'-methyl-4'-dimethylaminophenylsquaraine; 4-dimethylaminophenyl-2'-fluoro-4'-dimethylaminophenylsquaraine; and 4-dimethylaminophenyl-2'-methoxy-4'-dimethylaminophenylsquaraine.

The above members were then tested for photosensitivity in the visible infrared region of the spectrum by negatively charging the devices with a corona to −800 volts, followed by simultaneously exposing each member to monochromic light from a tungsten lamp in the wavelength region of about 400 to about 900 nanometers. The photoresponsive devices had excellent response, that is the devices discharged from −800 volts to about a −100 volts at 25 ergs/cm$^2$ in the wavelength region of from about 400 to about 900 nanometers, indicating both visible and infrared photosensitivity for these members.

With further respect to the process of the present invention, other specific reactants, reaction parameters, and the like may be selected, therefore, the present invention is not limited to the specific or other embodiments mentioned herein providing, for example, the desired products are obtained.

Other modifications of the present invention will occur to those skilled in the art subsequent to a review of the present application. These modifications, and equivalents thereof are intended to be included within the scope of this invention.

What is claimed is:

1. A photoconductive imaging member comprised of a photogenerating layer comprised of the squaraine compounds obtained by a process which comprises a cycloaddition, reduction alkylation and condensation reaction wherein there is reacted a nitroarylacetyl halide with a tetraalkoxy olefin and a trialkylamine in a solvent, followed by the reaction of the resulting nitroaryl dione with hydrogen in the presence of an aldehyde and a catalyst in a solvent; and thereafter reacting the formed dialkylaminoaryl hydroxycyclobutene dione with N,N-dialkylaniline in an alcohol, and a hole transport layer.

2. A photoconductive imaging member in accordance with claim 1 containing a supporting substrate.

Figure 1:
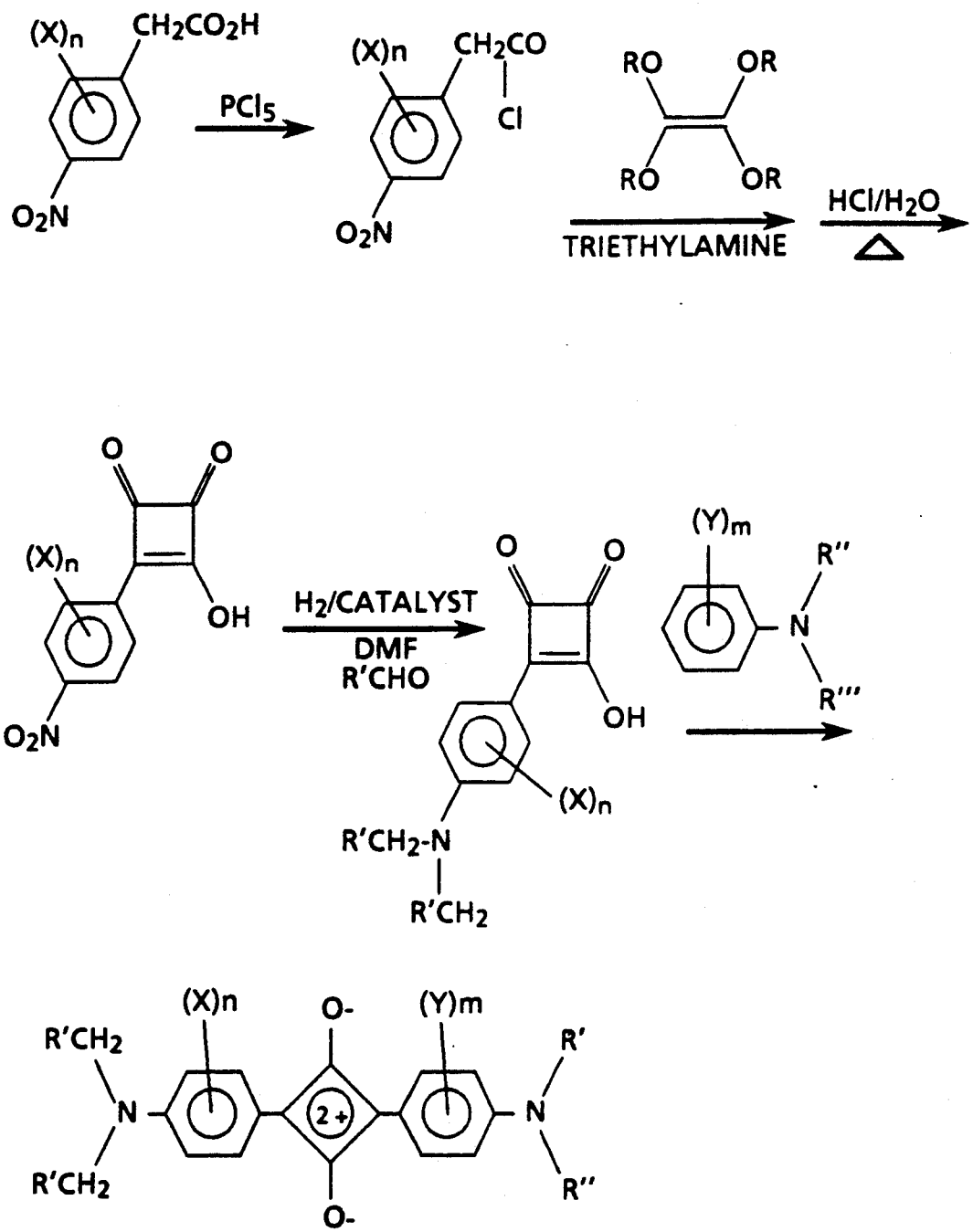
FIGS. 1 and 2 represent reaction schemes 1 and 2.

3. A photoconductive imaging member comprised of a hole transport layer, and a photogenerating layer comprising the squaraine compounds and wherein the aforementioned squaraine compounds are obtained by the process as illustrated by the reaction scheme of FIG. 1 wherein X and Y are independently selected from the group consisting of hydrogen, halide, alkyl, alkoxy, and hydroxy; n and m are the numbers 0 (zero), 1, 2 or 3; and R, R', R" and R'" are alkyl groups.

4. A photoconductive imaging member comprised of a hole transport layer, and a photogenerating layer comprising the squaraine compounds obtained by a process which comprises a cycloaddition, reductive alkylation and condensation reaction of a nitroarylacetyl halide with a tetraalkoxyethylene and a trialkylamine, followed by the reaction of the resulting nitroaryl dione with hydrogen in the presence of an aldehyde and a catalyst, and thereafter reacting the formed dialkylaminoaryl dione product with a dialkyl aniline.

5. A photoconductive imaging member in accordance with claim 3 containing a supporting substrate.

6. A photoconductive imaging member in accordance with claim 3 wherein the photogenerating layer is situated between the supporting substrate and the hole transport layer.

7. A photoconductive imaging member in accordance with claim 3 wherein the photoconductive imaging member contains a metal oxide or nylon hole blocking layer situated between the supporting substrate and the photogenerating layer.

8. A photoconductive imaging member in accordance with claim 7 wherein the metal oxide hole blocking layer has a thickness of less than about 500 Angstroms, and the nylon layer has a thickness of from about 0.1 to about 2.0 microns.

9. An imaging member in accordance with claim 1 wherein the hole transport layer is comprised of an aryl amine of the formula

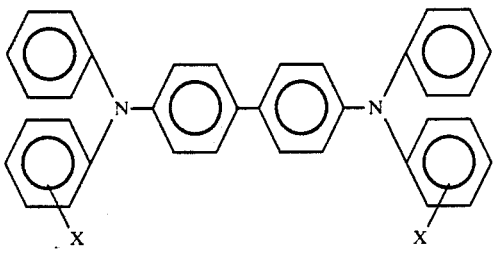

dispersed in a highly insulating and transparent organic resinous binder wherein X is selected from the group consisting of alkyl and halogen.

10. A photoconductive imaging member in accordance with claim 1 wherein the squaraine compound or hole transport is dispersed in a resinous binder.

11. A photoconductive imaging member in accordance with claim 10 wherein the resinous binder is a polyester, polyvinyl butyral, a polycarbonate, or polyvinyl formal.

12. A photoconductive imaging member in accordance with claim 3 wherein the aryl amine comprises molecules of the formula:

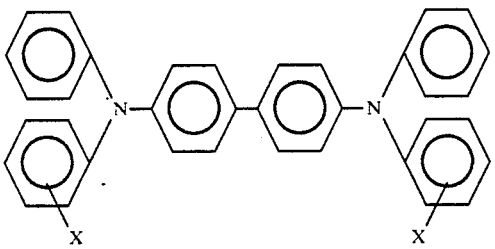

dispersed in a highly insulating and transparent organic resinous binder wherein X is selected from the group consisting of alkyl and halogen.

13. A photoconductive imaging member in accordance with claim 2 wherein the imaging member exhibits a dark development potential of from about −500 to about −1,000 volts.

14. A photoconductive imaging member in accordance with claim 2 wherein the imaging member exhibits a dark decay of from about −5 to about −100 volts per second.

15. A method of imaging which comprises the steps of:
(a) generating an electrostatic image on the photoconductive imaging member of claim 2,
(b) subsequently developing the electrostatic image;
(c) transferring the developed electrostatic image to a suitable substrate; and
(d) permanently affixing the transferred image to the substrate.

16. A method of imaging in accordance with claim 15 wherein the electrostatic image is developed by cascade, touchdown, powder cloud, or magnetic brush methods.

17. A method of imaging in accordance with claim 15 wherein the developed electrostatic image is transferred to a substrate by means of a corotron or a biased roll.

18. A method of imaging in accordance with claim 15 wherein the substrate is paper.

19. An imaging member in accordance with claim 11 wherein there are selected as the squaraine compounds for the photogenerating layer comprising a supporting substrate those represented by the formula

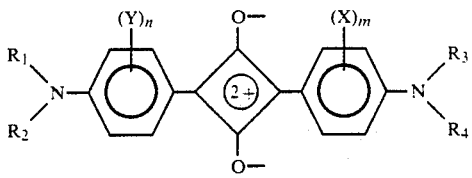

wherein $R_1$, $R_2$, $R_3$ and $R_4$ are independently selected from alkyl groups; X and Y are hydrogen, hydroxy, alkyl, alkoxy, or halogen; n is a number of from 0 to about 3; and m is a number of from 0 to about 2.

Figure 2:
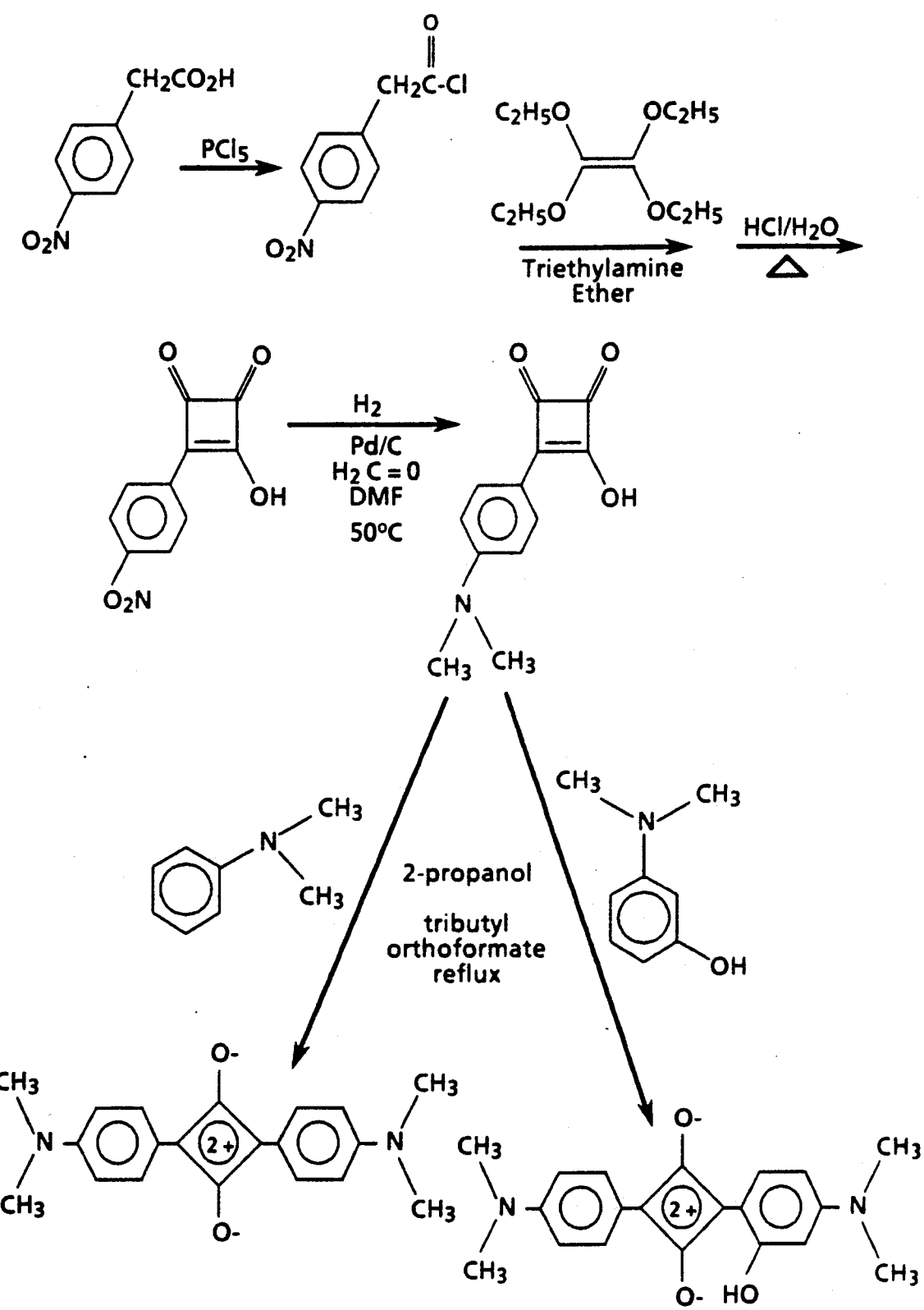

20. A photoconductive imaging member comprised of a supporting substrate, a photogenerating layer obtained by the process of reaction scheme 2 as illustrated in FIG. 2 and a hole transport layer.

21. An imaging member in accordance with claim 1 wherein the squaraine is 4-dimethaminophenyl-2′-methyl-4′-dimethylaminophenyl squaraine, 4-dimethaminophenyl-2′-hydroxy-4′-dimethylaminophenyl squaraine, 4-dimethaminophenyl-2′-fluoro-4′-dimethylaminophenyl squaraine, 4-dimethaminophenyl-2′-methoxy-4′-dimethylaminophenyl squaraine, or bis(4-dimethylaminophenyl)squaraine.

22. A photoconductive imaging member comprised of a photogenerating layer comprised of a squaraine compound obtained by a process which comprises reacting a nitroarylacetyl halide with a tetraalkoxy olefin and a trialkylamine in a solvent; followed by the reaction of the resulting nitroaryl dione with hydrogen in the presence of an aldehyde and a catalyst in a solvent; and thereafter reacting the formed dialkylaminoaryl hydroxycyclobutene dione with N,N-dialkylaniline in an alcohol, and a hole transport layer.

23. A process for the preparation of a layered photoconductive imaging member which comprises providing a supporting substrate and applying thereto a photogenerating layer and a hole transport layer wherein the photogenerating layer is comprised of a squaraine compound obtained by a process which comprises reacting a nitroarylacetyl halide with a tetraalkoxy olefin and a trialkylamine in a solvent; followed by the reaction of the resulting nitroaryl dione with hydrogen in the presence of an aldehyde and a catalyst in a solvent; and thereafter reacting the formed dialkylaminoaryl hydroxycyclobutene dione with N,N-dialkylaniline in an alcohol, and a hole transport layer.

* * * * *